(12) United States Patent
Winslow et al.

(10) Patent No.: US 10,610,381 B2
(45) Date of Patent: Apr. 7, 2020

(54) PATIENT SPECIFIC RECONSTRUCTIVE GLENOID SYSTEMS AND METHODS

(71) Applicant: Biomet Manufacturing, LLC, Warsaw, IN (US)

(72) Inventors: Nathan A. Winslow, Warsaw, IN (US); Michael Francis Kovacs, Warsaw, IN (US); John Schulz, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 239 days.

(21) Appl. No.: 15/886,944

(22) Filed: Feb. 2, 2018

(65) Prior Publication Data

US 2018/0280148 A1 Oct. 4, 2018

Related U.S. Application Data

(60) Provisional application No. 62/478,733, filed on Mar. 30, 2017.

(51) Int. Cl.
*A61F 2/30* (2006.01)
*A61B 17/16* (2006.01)
(Continued)

(52) U.S. Cl.
CPC ........ *A61F 2/4612* (2013.01); *A61B 17/1684* (2013.01); *A61F 2/30942* (2013.01); *A61F 2/4081* (2013.01); *A61B 17/1604* (2013.01); *A61B 17/92* (2013.01); *A61B 2017/922* (2013.01); *A61F 2002/2839* (2013.01); *A61F 2002/30957* (2013.01); *A61F 2002/30963* (2013.01); *A61F 2002/4615* (2013.01);
(Continued)

(58) Field of Classification Search
CPC ... A61F 2/30942; A61F 2/4612; A61F 2/4081
See application file for complete search history.

(56) References Cited

U.S. PATENT DOCUMENTS 3,835,860 A * 9/1974 Garretson .......... A61B 17/1611
606/79
4,990,161 A * 2/1991 Kampner ............ A61F 2/30767
623/18.11
(Continued)

FOREIGN PATENT DOCUMENTS

| EP | 1952788 | 8/2008 |
|---|---|---|
| WO | 2013062850 | 5/2013 |
| WO | 2018182849 | 10/2018 |

OTHER PUBLICATIONS

"International Application Serial No. PCT US2018 016556, Invitation to Pay Add'l Fees and Partial Search Report dated May 11, 2018", 14 pgs.
(Continued)

*Primary Examiner* — Christian A Sevilla
(74) *Attorney, Agent, or Firm* — Schwegman Lundberg & Woessner, P.A.

(57) ABSTRACT

A system for repairing a glenoid defect of a specific patient can include a patient-specific punch and a patient-specific shaping block. The patient-specific punch can form a patient-specific glenoid implant from a bone puck. The patient-specific shaping block can shape the patient-specific glenoid implant to match and fill a glenoid defect of a specific patient.

20 Claims, 8 Drawing Sheets

(51) Int. Cl.
  *A61F 2/40* (2006.01)
  *A61F 2/46* (2006.01)
  *A61F 2/28* (2006.01)
  *A61B 17/92* (2006.01)
(52) U.S. Cl.
  CPC ............ *A61F 2002/4649* (2013.01); *A61F 2002/4681* (2013.01)

(56) References Cited

U.S. PATENT DOCUMENTS

| | | | | |
|---|---|---|---|---|
| 5,282,866 | A | * | 2/1994 | Cohen ................ A61B 17/1604 623/20.34 |
| 9,173,665 | B2 | | 11/2015 | Couture |
| 2007/0055380 | A1 | * | 3/2007 | Berelsman ............ A61F 2/4081 623/19.11 |
| 2007/0093896 | A1 | | 4/2007 | Malinin |
| 2007/0219637 | A1 | * | 9/2007 | Berelsman ............ A61F 2/4081 623/19.11 |
| 2011/0106093 | A1 | * | 5/2011 | Romano ............... A61B 17/155 606/88 |
| 2012/0078259 | A1 | * | 3/2012 | Meridew ............ A61B 17/1746 606/87 |
| 2014/0276231 | A1 | | 9/2014 | Wood |
| 2015/0012104 | A1 | | 1/2015 | Boileau et al. |
| 2016/0345987 | A1 | | 12/2016 | Guilloux et al. |

OTHER PUBLICATIONS

"International Application Serial No. PCT US2018 016556, International Preliminary Report on Patentability dated Oct. 10, 2019", 11 pgs.

* cited by examiner

PATIENT SPECIFIC RECONSTRUCTIVE GLENOID SYSTEMS AND METHODS

PRIORITY APPLICATIONS

This application claims the benefit of priority to U.S. Provisional Patent Application Ser. No. 62/478,733, filed Mar. 30, 2017, the content of which is hereby incorporated by reference in its entirety.

BACKGROUND

In some shoulder surgeries, the glenoid bone is used to anchor one or more fasteners. Sometimes a patient's glenoid has one or more defects that can reduce the available screw purchase at the glenoid. Some current practices for addressing a glenoid defect can involve lengthy processes, difficult procedures, removing too much of the glenoid, compromising the glenoid vault, or the like. Further, some current practices do not effectively correct the defect, are unable to address a defect interior to the peripheral edge of the glenoid, can create an irregular geometry within the shoulder joint, or the like.

OVERVIEW

To better illustrate the instrument disclosed herein, a non-limiting list of examples is provided here:

In Example 1, a system can be provided for repairing a glenoid defect of a specific patient, the system can include an impactor body, and a patient-specific punch coupled to the impactor body, the patient-specific punch including a patient-specific void corresponding to the glenoid defect, is optionally configured such that the impactor body is configured to drive the patient-specific punch into an implant material to form a patient-specific glenoid implant.

In Example 2, the system of Example 1 is optionally configured such that the patient-specific punch can be removably coupled to the impactor body.

In Example 3, the system of Example 1 or 2 is optionally configured such that the implant material can include a bone puck formed from a resected portion of a humeral head.

In Example 4, they system of any of Examples 1-3 is optionally configured such that the patient-specific glenoid implant can be configured to be coupled to a base plate that is configured to be coupled to the glenoid.

In Example 5, the system of Example 4 can optionally include a patient-specific shaping block configured to receive the patient-specific glenoid implant in a shaping void, and a spacer configured for placement in the patient-specific shaping block, the spacer having a geometry corresponding to the base plate, the system is optionally configured such that the shaping void is configured to match the glenoid defect, the system is optionally configured such that the patient-specific glenoid implant is configured to be impacted such that the shaping void and the spacer shape the patient-specific glenoid implant to repair the glenoid defect.

In Example 6, the system of Example 5 can optionally include an impactor head configured to be removably coupled to the impactor body.

In Example 7, the system of Example 5 or 6 is optionally configured such that the patient-specific shaping block can further include a cover, the cover configured to receive a guide pin.

In Example 8, the system of any of Examples 5-7 can optionally include a base plate reamer configured to ream the patient-specific glenoid implant to match features of the base plate.

In Example 9, the system of any of Examples 1-8 is optionally configured such that the patient-specific punch can include knifed edges.

In Example 10, a system can be provided for repairing a glenoid defect of a specific patient, the system can include a patient-specific punch including a patient-specific void corresponding to the glenoid defect, the patient-specific punch configured to form a patient-specific glenoid implant, and a patient-specific shaping block configured to receive the patient-specific glenoid implant in a shaping void that matches the glenoid defect, the system is optionally configured such that the patient-specific glenoid implant is configured to be impacted such that the shaping void shapes the patient-specific glenoid implant to fill the glenoid defect.

In Example 11, the system of Example 10 can optionally include a base plate configured to be coupled to the patient-specific glenoid implant for implantation in the specific patient.

In Example 12, the system of Example 11 can optionally include a spacer configured to be inserted into the patient-specific shaping block, the spacer having a geometry corresponding to the base plate.

In Example 13, the system of any of Examples 10-12 can optionally include a bone cutter configured to form a bone puck, is optionally configured such that the patient-specific punch is configured to impact the bone puck to form the patient-specific glenoid implant.

In Example 14, the system of Example 13 is optionally configured such that the bone cutter can optionally include an extraction block configured to receive a humeral head resection, a fastener configured to extend through the humeral head resection, and a rotatable blade assembly configured to be received by, and rotate around, the fastener to cut the humeral head resection to form the bone puck.

In Example 15, the system of any of Examples 10-14 can optionally include an impactor body can include an attachment portion configured to be removably coupled to one or more attachments, the system is optionally configured such that the patient-specific punch is configured to be removably coupled to the attachment portion of the impactor body.

In Example 16, the system of Example 15 can optionally include an impactor head attachment configured to be removably coupled to the attachment portion of the impactor body.

In Example 17, a method can be provided for repairing a glenoid defect of a specific patient, the method can include driving a patient-specific punch into an implant material to create a patient-specific glenoid implant, the method is optionally configured such that the patient-specific punch can include a patient-specific void corresponding to the glenoid defect, placing the patient-specific glenoid implant in a patient-specific shaping block including a shaping void that matches the glenoid defect, and impacting the patient-specific glenoid implant, such that the patient-specific shaping block shapes the patient-specific implant to fill the glenoid defect.

In Example 18, the method of Example 17 can optionally include forming the bone puck from a resected portion of a humeral head.

In Example 19, the method of Example 17 or Example 18 can optionally include reaming the patient-specific implant to accommodate a base plate.

In Example 20, the method of Example 19 can optionally include coupling the patient-specific glenoid implant to the base plate that is configured to be coupled to the glenoid.

In Example 21, the system or method of any of Examples 1-20 can optionally be combined.

These and other examples and features of the present devices, systems, and methods will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
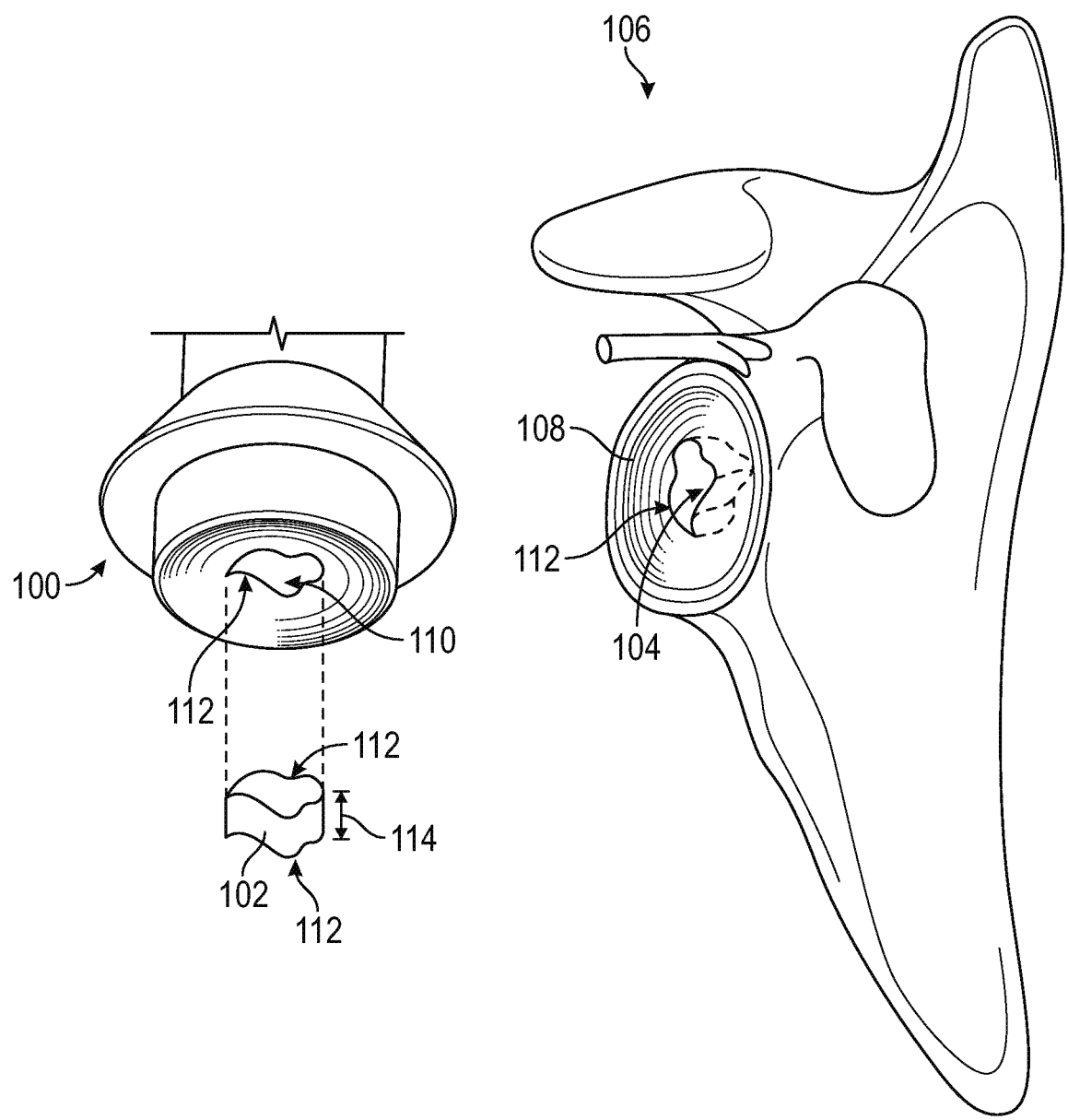
FIG. 1 is a perspective view of a patient-specific punch for forming a patient-specific glenoid implant corresponding to a glenoid defect of a specific patient, in accordance with at least one example of the present disclosure.

In some shoulder surgeries, defects in a patient's glenoid can affect the repair of the shoulder, since the glenoid can be used to anchor fasteners. These glenoid defects reduce the amount of available screw purchase between the base plate and the cortical or cancellous bone of the patient. Some current procedures attempt to counteract the effect of glenoid defects with bone substitutes and the use of cancellous bone fragments, but these processes are lengthy, difficult to place, and the bone fragments do not always fit the geometry of the glenoid defect's void since they are not patient-specific.

Current surgical options are limited for addressing a glenoid that has experienced a large magnitude of retroversion on the posterior rim of the glenoid (e.g., B2 Walch classification glenoid defects). Such defects allow the shoulder to be prone to subluxation through the posterior wall and could cause impingement within the muscular skeletal system. These defects come in a range of sizes and complex shapes, which leave little to no bone along the posterior rim of glenoid and can spread anteriorly.

One current technique involves reaming the face of the glenoid down the lateral surface to eliminate the existing retroversion, created by wear between the glenoid and humerus. Another current technique utilizes an augmented glenoid. Both of these current techniques involve taking a substantial amount of bone from the glenoid. The glenoid vault only has a certain amount of suitable bone before the vault is completely compromised. Some current techniques only address defects of the peripheral edge of the glenoid. Many of these techniques can create irregular geometry within the shoulder joint.

The present disclosure provides various systems and methods related to a patient-specific glenoid implant for filling the void of a glenoid defect of a specific patient. In at least one example, the present disclosure provides systems and methods for reconstructing the glenoid vault naturally utilizing autograft, allograft, bone substitute, or a combination of these. In at least one example, the resulting glenoid implant will be patient-matched and fixated to existing bone as the new bone grows. In at least one example, the systems and methods of the present disclosure allow a surgeon to match a specific glenoid void while reconstructing the glenoid rim and creating correct muscle tensioning. Further, in at least one example the systems and methods of the present disclosure allow for preoperative planning and preparation to reduce surgical time. In at least one example, the systems and methods of the present disclosure allow a surgeon to mitigate the risk of biocompatibility rejections, since the patient's body will be more accepting of an implant made from the patient's anatomy. While the present disclosure is described with reference to a glenoid repair, the systems and methods of the present disclosure could also be used for any bone defect repair.

For the purposes of this disclosure, patient-specific can be defined as including dimensions specific to an individual patient, such that the dimensions would differ from patient to patient. That is, a patient-specific glenoid implant can be custom to an individual patient's anatomy. In at least one example, patient-specific can be defined as comprising a geometry that matches the anatomy of the specific patient. In at least one example, patient-specific can be defined as comprising a geometry that mirrors the anatomy of a specific patient. In at least one example, patient-specific can be defined as comprising a geometry that exactly matches the geometry of a specific patient's anatomy. In at least one example, patient-specific can be defined as having a geometry that completely fills a void in a specific patient's anatomy. Patient-specific glenoid implants can allow for a more precise and successful repair of a glenoid defect.

FIG. 1 is a perspective view of a patient-specific punch 100 for forming a patient-specific glenoid implant 102 corresponding to a glenoid defect 104 of a specific patient 106, in accordance with at least one example of the present disclosure. The glenoid defect 104 can have any geometry and be located anywhere on the glenoid 108 of the patient 106. Further, in at least one example, the patient 106 can have multiple glenoid defects, and each glenoid defect can be repaired separately with multiple patient-specific punches, or a single patient-specific punch can be created to address multiple glenoid defects.

The patient-specific punch 100 can include a patient-specific void 110 corresponding to the glenoid defect 104. In at least one example, the patient-specific void 110 can be defined by knifed or cutting edges. In some examples, the patient-specific void 110 can include a measured geometry of the glenoid defect. In at least one example, the patient-specific void 110 exactly matches the void of the glenoid defect 104 of the specific patient 106. In at least one example, the geometry of the glenoid defect 104 can be determined in any of a variety of manners, including patient imaging for example, X-ray, CT (computerized tomography), MRI (magnetic resonance imaging), pre-operative planning tools and the like. In at least one example, patient scans can be converted into three dimensional models to determine the three dimensional size and shape of the glenoid defect. In at least one example, segmentation of CT scans is used to determine the size and shape of the glenoid defect. The patient-specific punch 100 is formed for the specific patient. In at least one example, the patient-specific punch 100 would only match the geometry of the specific patient for which it was created.

In at least one example, the patient-specific punch 100 can include a patient-specific void 110 that matches specific dimensions of the glenoid defect 104, but does not exactly match the entire geometry of the glenoid defect 104. For example, the patient-specific void 110 can match a two-dimensional outline 112 of the glenoid defect 104, such that the patient-specific punch 100 can form a patient-specific glenoid implant 102 that includes the dimensions of the outline 112 but continues those dimensions for a fixed height 114. In other examples, the patient-specific punch 100 can include a patient-specific void 110 that matches different selected portions of the geometry of the glenoid defect 104.

In some examples, the patient-specific punch 100 can be driven into an implant material to form the patient-specific glenoid implant 102. In some examples, the implant material can comprise bone. In at least one example, the implant can comprise an allograft. In some examples, the implant material can comprise an autograft. In at least one example, the implant material can comprise a resected humeral head portion of the specific patient 106. In some examples, the implant material can comprise cancellous bone.

Figure 2A:
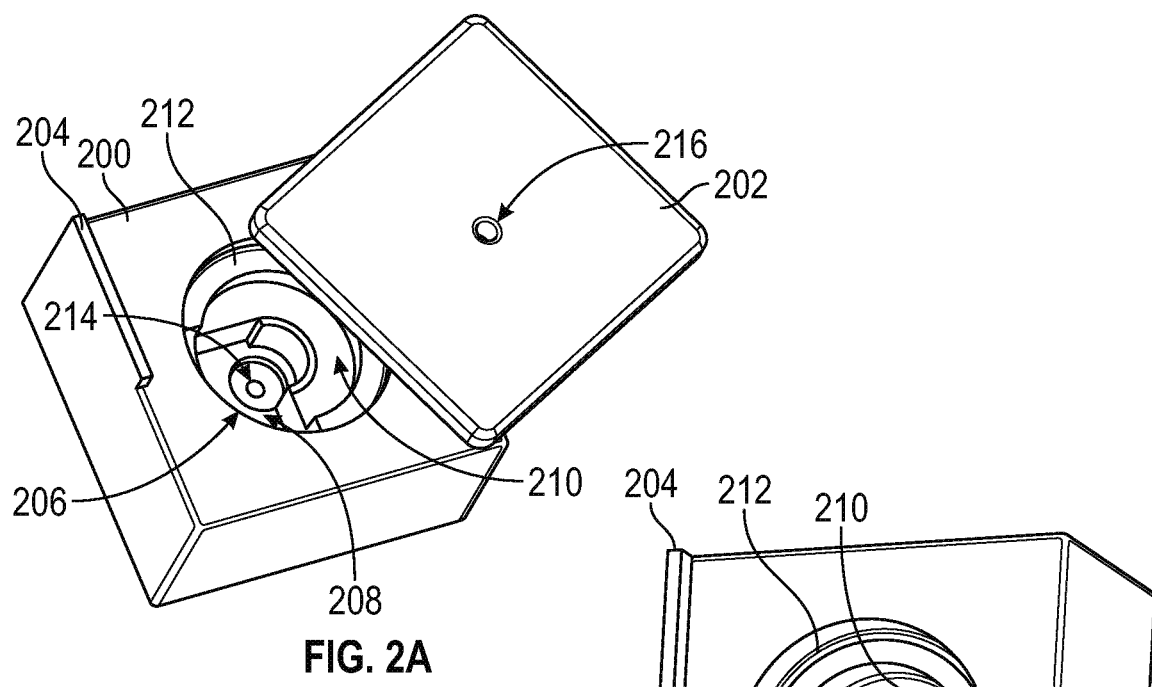
FIG. 2A is a perspective view of a patient-specific shaping block for shaping the patient-specific glenoid implant, in accordance with at least one example of the present disclosure.

FIG. 2A is a perspective view of a patient-specific shaping block 200 for shaping the patient-specific glenoid implant 102, in accordance with at least one example of the present disclosure. In some examples, the patient-specific shaping block 200 can include a cover 202 configured to be placed over the patient-specific shaping block 200. In at least one example, the box can include one or more lid features 204 configured to interact with the cover 202 to seat, center, or secure the cover 202 on the block 200.

In some examples, the patient-specific shaping block 200 can include a block void 206. In at least one example, the block void 206 can include a patient-specific portion corresponding to the glenoid defect 104 of the specific patient 106. In at least one example, the patient-specific portion 208 can match the geometry of the glenoid defect 104. In some examples, the block void 206 can further include a base plate portion 210 corresponding to a base plate, for example, a base plate used during shoulder surgery. In some examples, the block void 206 can include an impactor seat 212 configured to receive an impactor head during impaction. In some examples, the cover 202 can be configured to receive the impactor head and can include one or more features to transfer the impact to the patient-specific glenoid implant 102.

In some examples, the patient-specific shaping block 200 can include one or more fastener holes 214 for receiving a fastener. In at least one example, the cover 202 can include one or more fastener holes 216 corresponding to one or more fastener holes 214 of the patient-specific shaping block 200. In some examples, the fastener can comprise a pin, a drill bit, a wire, or the like. In at least one example, the fastener can comprise a 3.2 mm diameter Steinman pin. In at least one example, the cover 202 can receive a 3.2 mm Steinman pin to be placed in the center of the glenoid post which can allow for accurate reaming and similarities between the Comprehensive® Reverse Shoulder System and glenoid reconstruction techniques. In at least one example, the cover 202 can provide alignment for a drill or other tool. In at least one example, the cover 202 can be a drill guide. In at least one example, one or more tools can be cannulated, such that the one or more tools be slid over the pin for controlled alignment. In at least one example, the patient-specific shaping block 200 can be used to shape the patient-specific glenoid implant 102 created by the patient-specific punch 100.

Figure 2B:
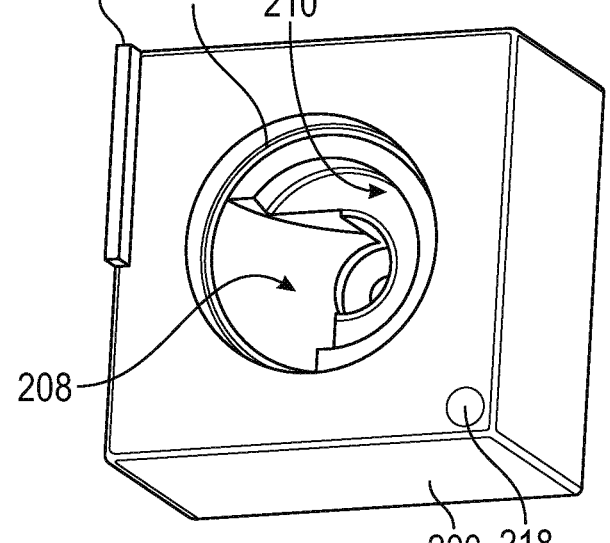
FIG. 2B is another perspective view of the patient-specific shaping block of FIG. 2A, in accordance with at least one example of the present disclosure.

FIG. 2B is another perspective view of the patient-specific shaping block 200 without the cover 202, in accordance with at least one example of the present disclosure. In the illustrated example, the patient-specific shaping block 200 can include a lid attachment feature 218. In some examples, the lid attachment feature 218 can be a pin about which the cover 202 can pivot. In some examples, the lid attachment feature 218 can include any of a variety of alignment features, for example, peg, hole, tab, latch, slot, etc. In at least one example, the lid attachment feature 218 can be a press-fit feature. In at least one example, the lid attachment feature 218 can comprise a hinge point. In some examples, the cover 202 can include a corresponding attachment feature that corresponds to the lid attachment feature 218. In at least one example, the patient-specific shaping block 200 does not include the cover 202.

Figure 2C:
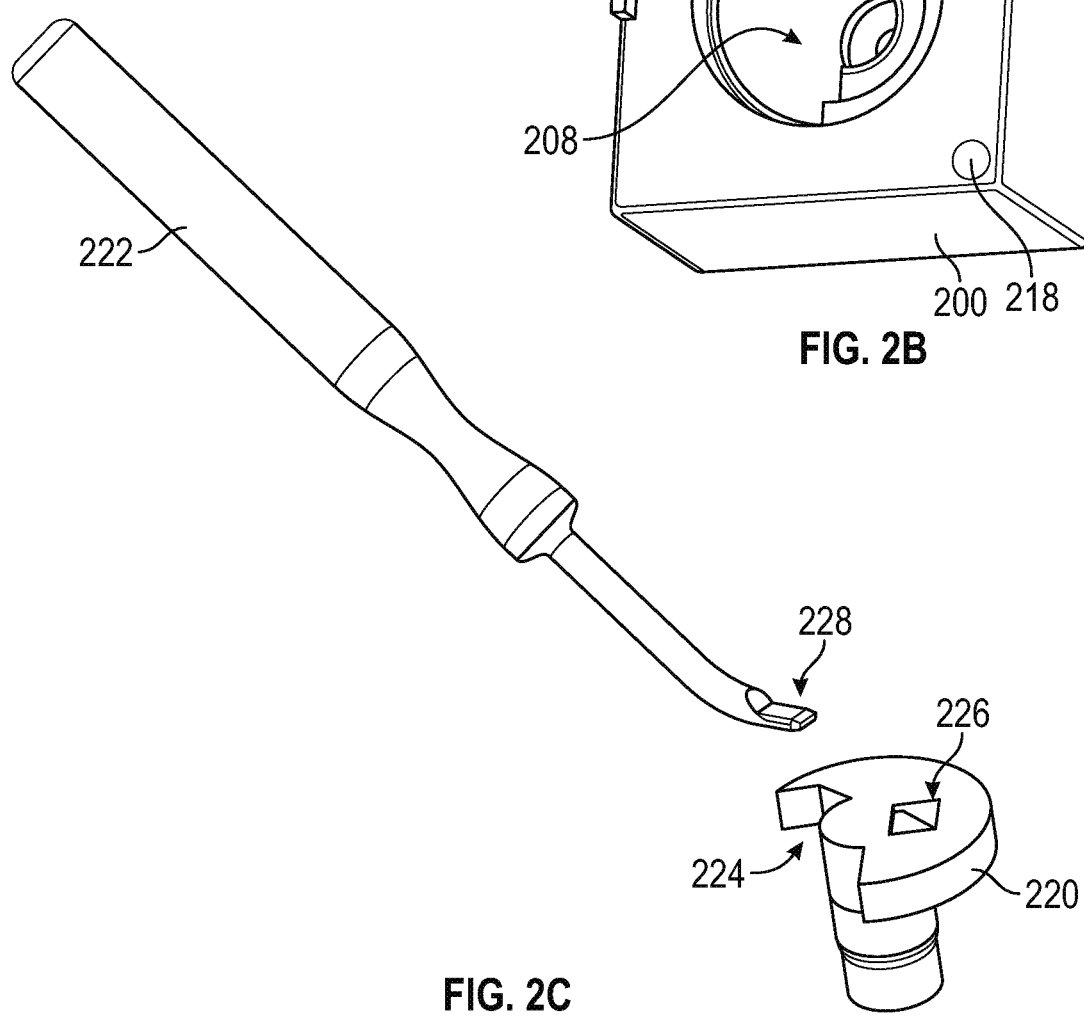
FIG. 2C is a perspective view of a spacer and a spacer removal tool, in accordance with at least one example of the present disclosure.

FIG. 2C is a perspective view of a spacer 220 and a spacer removal tool 222, in accordance with at least one example of the present disclosure. In at least one example, the spacer 220 can match the geometry of the base plate, such that the spacer 220 can shape the patient-specific glenoid implant 102 to fit the base plate. In at least one example, the spacer 220 can ensure the patient-specific glenoid implant 102 takes the shape needed to fill the void of the glenoid defect 104. In some examples, the spacer 220 can include a defect feature 224 to allow space for the patient-specific glenoid implant 102 in the patient-specific shaping block 200. In at least one example, the defect feature 224 can be patient-specific.

In some examples, the spacer 220 can include a removal feature 226, such that a removal portion 228 of the removal tool 222 can interact with the removal feature 226 to remove the spacer 220 from the patient-specific shaping block 200. In at least one example, the removal feature 226 can allow for removal of the spacer 220 without the use of a specific spacer removal tool 222. While in the illustrated example the removal feature 226 comprises a recess that receives the removal portion 228 of the removal tool 222, in other examples, the removal feature 226 and the removal portion 228 can include any features that interact for removal of the spacer 220 from the patient-specific shaping block 200. In at least one example, the spacer removal tool 222 can create a lever arm when interacting with the spacer 220 to pop the spacer 220 out of the patient-specific shaping block 200.

Figure 2D:
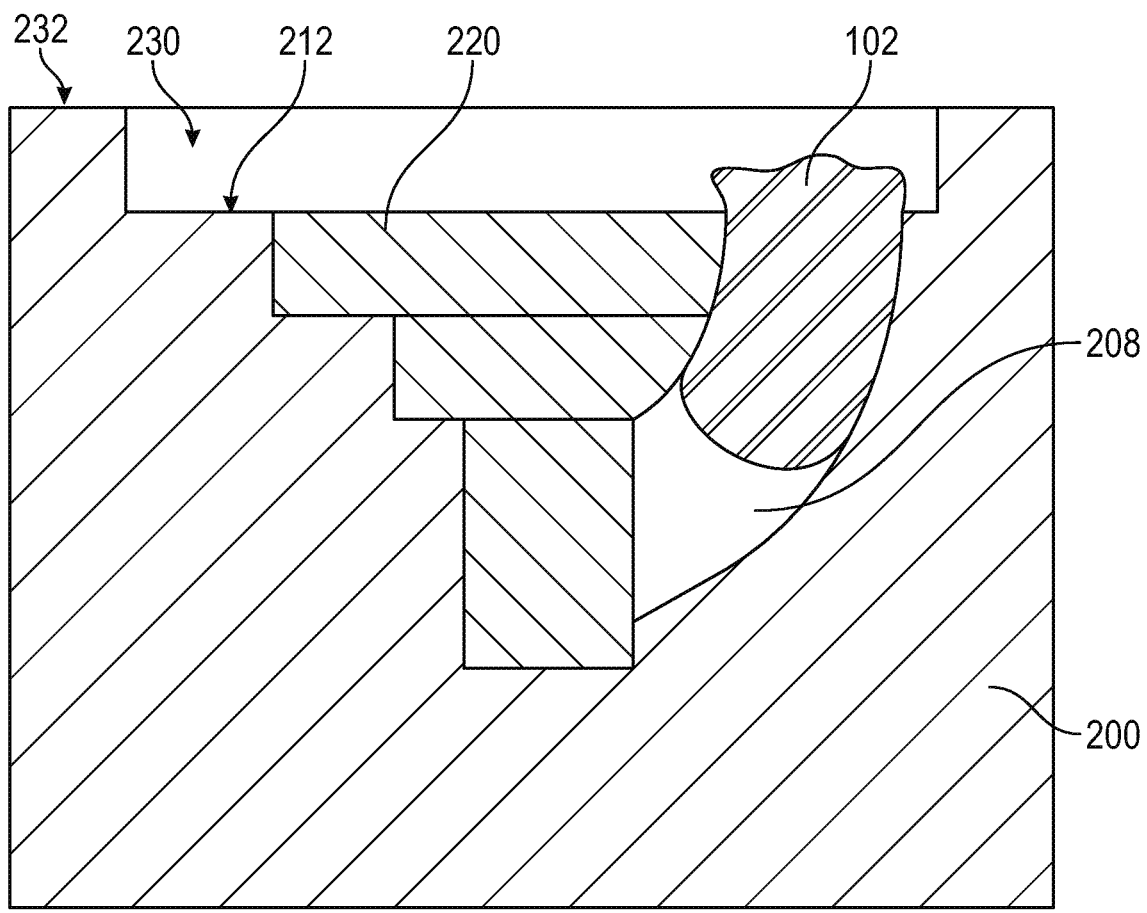
FIG. 2D is a cross-section view of a spacer inserted into a patient-specific shaping block to shape a patient-specific glenoid implant, in accordance with at least one example of the present disclosure.

FIG. 2D is a cross-section view of the spacer 220 inserted into the patient-specific shaping block 200 to shape the patient-specific glenoid implant 102, in accordance with at least one example of the present disclosure. In the illustrated example, the patient-specific glenoid implant 102 can extend into impactor space 230 between the impactor seat 212 and a top surface 232 of the patient-specific shaping block 200. In at least one example, an impactor can be used to apply force to the patient-specific glenoid implant 102, such that the patient-specific glenoid implant 102 fills the patient-specific portion 208 of the block void 206 to match the geometry of the glenoid defect 104 while accommodating the base plate. After the patient-specific glenoid implant 102 has been impacted to fill the patient-specific portion 208 of the block void 206, the spacer 220 can be removed with the spacer removal tool 222 or otherwise, and the patient-specific glenoid implant 102 can be prepared for implantation in the glenoid defect 104 of the specific patient 106. In at least one example, the spacer 220 can control critical features when impacting the patient-specific glenoid implant 102 made, for example, of cancellous bone. In at least one example, the spacer 220 can have the geometry of the Comprehensive® Reverse Shoulder System base plate to ease the reaming process needed for implanting a Comprehensive® Reverse Shoulder System base plate with the patient-specific glenoid implant 102. In at least one example, the spacer 220 can have the geometry of the Trabecular Metal™ Reverse Shoulder System base plate to ease the reaming process needed for implanting a Trabecular Metal™ Reverse Shoulder System base plate with the patient-specific glenoid implant 102.

Figure 3A:
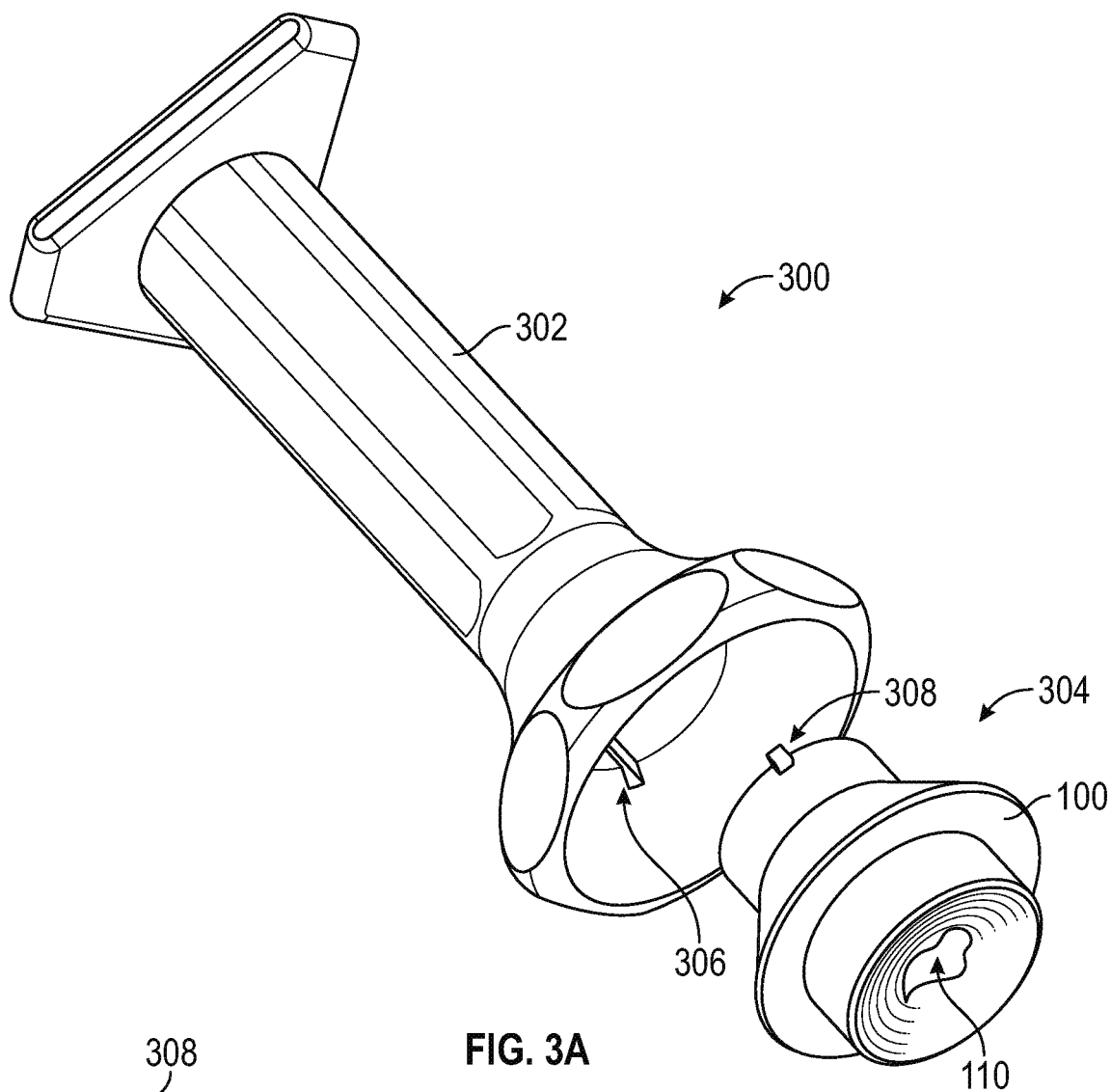
FIG. 3A is a perspective view of an impactor body and a patient-specific punch attachment, in accordance with at least one example of the present disclosure.

FIG. 3A is a perspective view of an impactor 300 in accordance with at least one example of the present disclosure. The impactor 300 can include an impactor body 302 and an impactor attachment 304. In the illustrated example, the impactor attachment 304 can comprise the patient-specific punch 100 of FIG. 1 including the patient-specific void 110. In at least one example, the impactor body 302 can include an attachment portion 306 configured to interact with one or more attachment features 308 of the impactor attachment 304. In at least one example, the attachment portion 306 of the impactor body 302 can allow one or more impactor attachments 304 to be removably coupled to the impactor body 302. In at least one example, the impactor body 302 can be used for multiple surgeries and multiple patients. In at least one example, some of the impactor attachments 304, such as the patient-specific punch 100, are patient-specific and can only be used for the specific patient 106 with which they correspond. In this manner, when the patient-specific punch 100 is no longer needed, it can be removed from the impactor body 302 and disposed of, but the impactor body 302 can still be used with other impactor attachment 304.

Figure 3B:
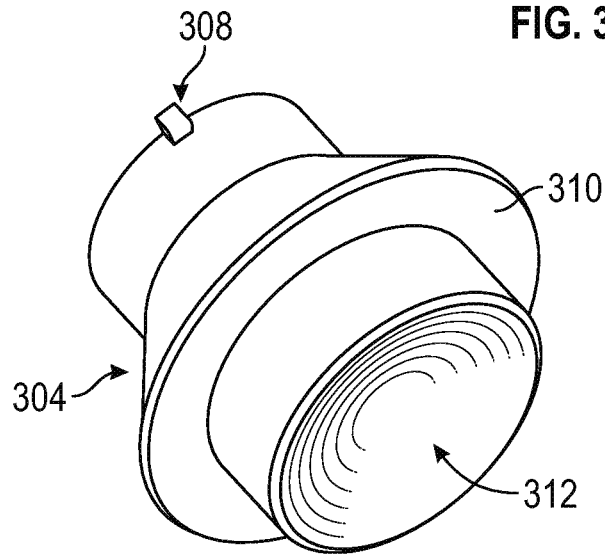
FIG. 3B is a perspective view of an impactor head attachment for the impactor body of FIG. 3A, in accordance with at least one example of the present disclosure.

FIG. 3B is a perspective view of another impactor attachment 304 in accordance with at least one example of the present disclosure. In at least one example, the impactor attachment 304 can include an impactor head attachment 310. In some examples, the impactor head attachment 310 can include one or more attachment features 308, such that the impactor head attachment 310 can be removably coupled to the impactor body 302. In at least one example, the impactor head attachment 310 can include a generic impactor face 312. In at least one example, the impactor head attachment 310 can be shaped and sized to fit within the impactor seat 212 of the patient-specific shaping block 200.

In at least one example, the impactor head attachment 310 can include one or more patient-specific features to facilitate shaping of the patient-specific glenoid implant 102 to fill the glenoid defect 104.

Figure 4:
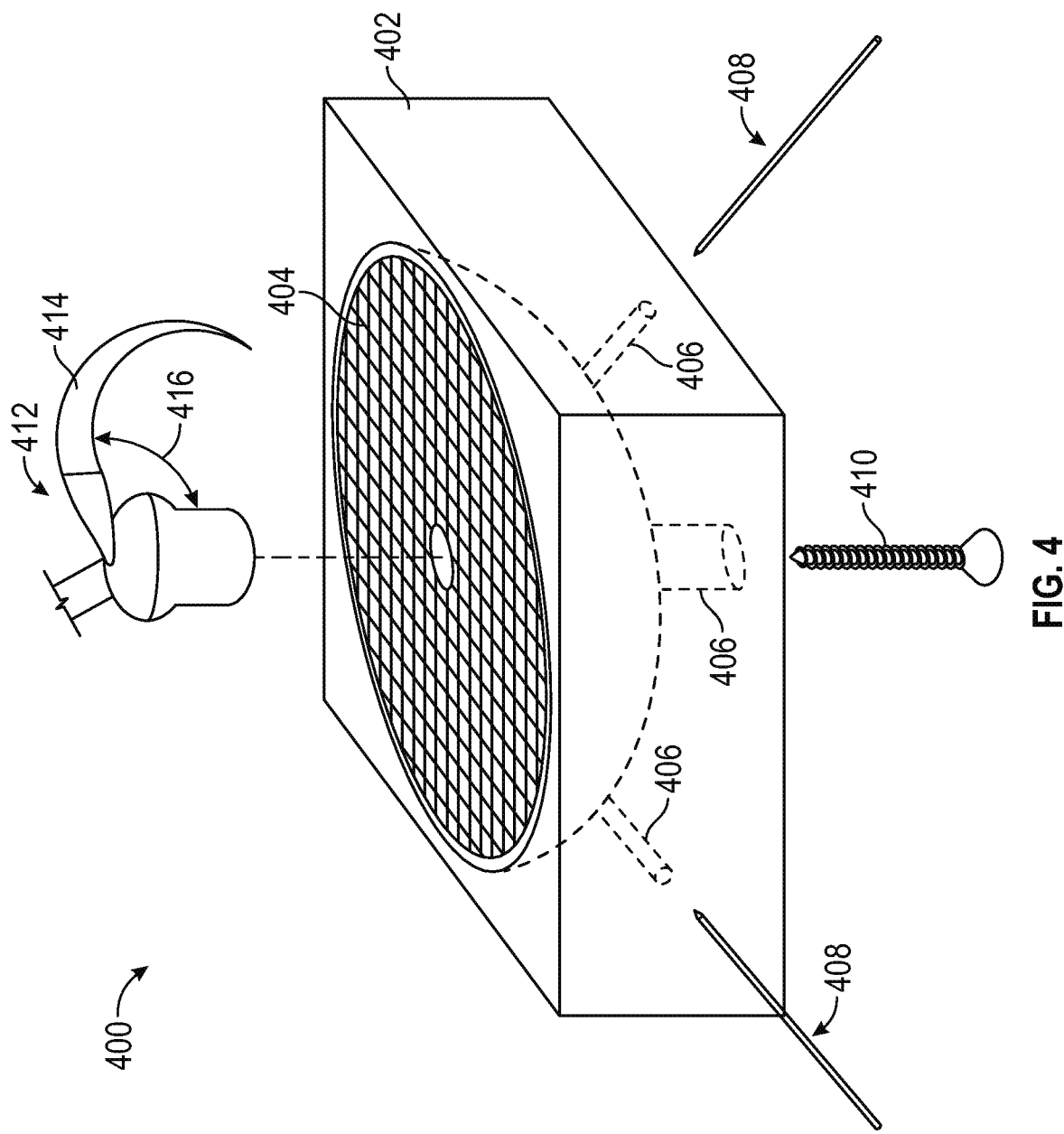
FIG. 4 is a perspective view of a bone cutter, in accordance with at least one example of the present disclosure.

FIG. 4 is a perspective view of a bone cutter 400, in accordance with at least one example of the present disclosure. In some examples, the bone cutter 400 can include an extraction block 402 configured to receive an implant material 404. In some examples, the implant material 404 can comprise an allograft. In at least one example, the implant material 404 can comprise an autograft. In at least one example, the implant material 404 can comprise a resected humeral head. In some examples, the bone cutter 400 can include one or more fastener apertures 406, each configured to receive a fastener, for example a pin 408, a screw 410, or the like. In at least one example, one or more of the fasteners 408, 410 can be configured to be driven into the implant material 404.

In some examples, the bone cutter 400 can include a rotatable blade assembly 412. In at least one example, the blade assembly 412 can be coupled to the fastener 410 driven through the extraction block 402 and the implant material 404. In at least one example, the blade assembly 412 can be coupled to the implant material 404. In at least one example, the blade assembly 412 can be coupled to the extraction block 402. In some examples the blade assembly 412 can include one or more arcuate blades 414. In at least one example, the blade 414 can comprise an explant knife. In some examples, a user can place the implant material 404 in the extraction block 402, insert the fasteners 408, 410, and attach the blade assembly 412. In at least one example, the implant material can comprise a resected humeral head, which can be placed into the extraction block 402 cortical side first. In at least one example, after the blade assembly is attached, the blade assembly 412 can be rotated to cut the implant material 404 to form a bone puck. In some examples, the blade 414 can pivot within a range 416, for example 30 degrees to allow the changes in the angle of the blade 414. In at least one example, the pivot range 416 can facilitate entry of the blade 414 into the implant material 404. In at least one example, the pivot range 416 can allow the cut of the blade 414 to cater to the natural anatomical shape of the humeral head, which can allow the surgeon to maximize the amount of available bone, which can give the surgeon a better chance at being able to address the defect by giving them more cancellous material to work with. In at least one example, the blade assembly 412 can be set to a predetermined depth, such that the blade 414 will only cut to the predetermined depth to create the bone puck shape needed by the surgeon. In at least one example, the bone cutter 400 can create a cone-shaped bone puck.

In at least one example, the patient-specific punch 100 (FIG. 1) can impact the bone puck to form the patient-specific glenoid implant 102. In at least one example, the patient-specific glenoid implant 102 can then be placed in the patient-specific shaping block 200 with the spacer 220 and impacted to shape the patient-specific glenoid implant 102. In some examples, the patient-specific glenoid implant 102 will then perfectly match the glenoid defect 104 of the specific patient 106 and can be implanted into the glenoid defect 104 of the specific patient 106. In at least one example, the patient-specific glenoid implant 102 can be reamed to facilitate implantation. In at least one example, the patient-specific implant 102 can be coupled to the base plate before being implanted into the anatomy of the specific patient 106. In at least one example, the base plate can be coupled to the patient-specific implant 102 with a peripheral screw.

Figure 5:
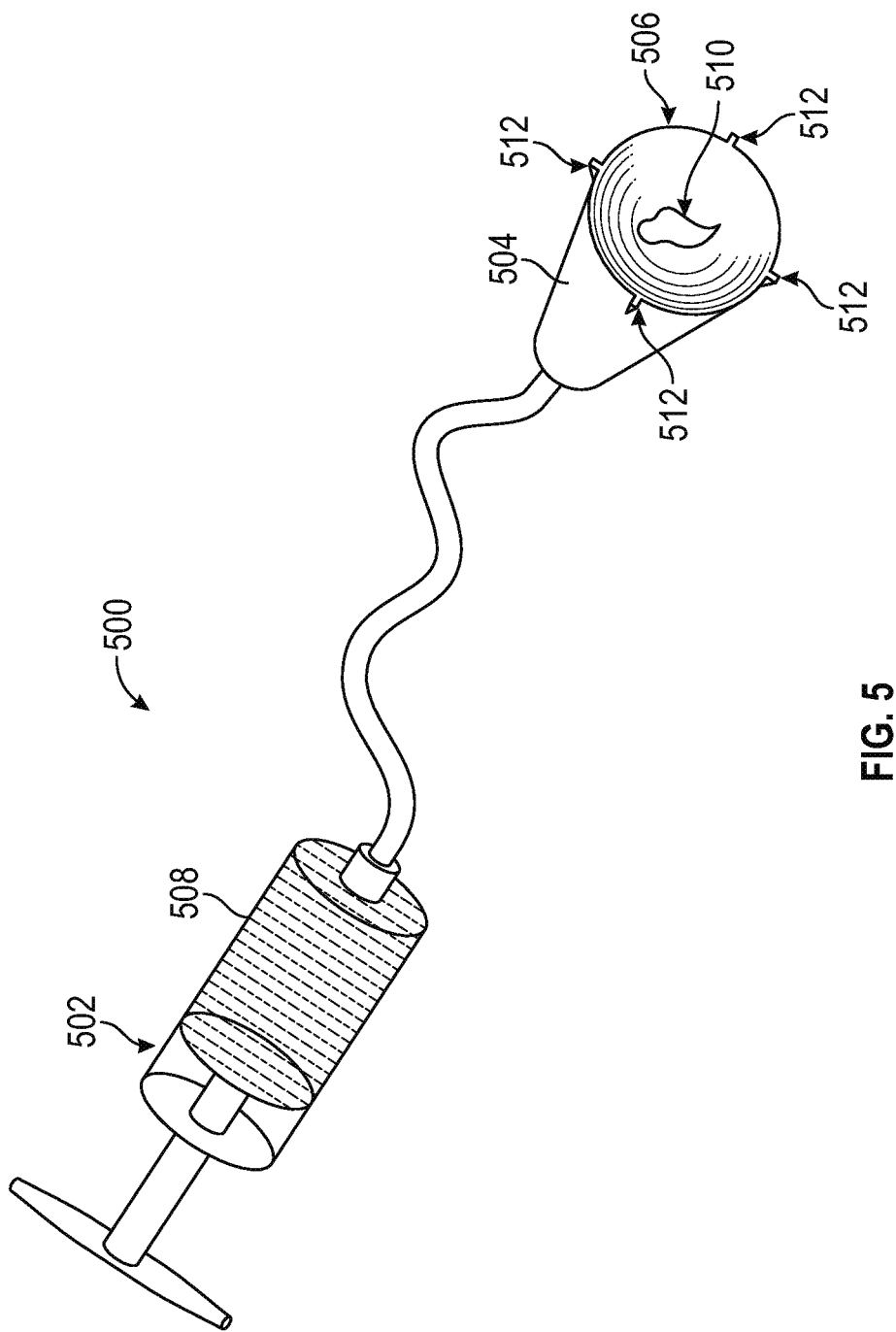
FIG. 5 is a perspective view of a patient-specific bone substitute injector, in accordance with at least one example of the present disclosure.

FIG. 5 is a perspective view of a patient-specific bone substitute injector 500, in accordance with at least one example of the present disclosure. In at least one example, the patient-specific bone substitute injector 500 can include an injector 502, a nozzle 504, and a patient-specific portion 506. In at least one example, the patient-specific portion 506 can comprise a patient-specific glenoid sleeve that can be placed over the face of the glenoid defect 104. In at least one example, the glenoid sleeve concentrates bone substitute 508 to directly fill the glenoid defect 104 through a patient-specific feature 510. In at least one example, the glenoid sleeve constrains where the bone substitute can be injected such that it only fills the glenoid defect 104. In at least one example, the patient-specific portion 506 can include a vacuum seal adapter to attach to the glenoid sleeve to create a sealed lining around the glenoid 108. In at least one example, the patient-specific portion 506 can form a secure, semi-sealed fit with the glenoid 108. In at least one example, the patient-specific portion 506 can prevent bone substitute 508 from attaching to areas where it is not needed. In at least one example, the patient-specific portion 506 can be a cap coupled to the nozzle 506 with a patient-specific feature 510 to direct the bone substitute 508 into the glenoid defect 104. In at least one example, the patient-specific portion 506 can include one or more attachment features 512 to fit the patient-specific portion 506 over the glenoid 108 of the specific patient 106. In some examples, the patient-specific portion 506 can be fit over the glenoid 108 of the specific patient, and the injector 502 can inject bone substitute 508 to fill the glenoid defect 104, which can set to form the patient-specific implant 102 within the glenoid defect 104 of the specific patient 106. In at least one example, the patient-specific portion 506 can then be disposed of, while the injector 502 can be reused for subsequent surgeries or subsequent patients. For example, a new patient-specific portion (corresponding to a glenoid defect of a new patient) can be coupled to the injector 502 and the process can be repeated.

In at least one example, the patient-specific bone substitute injector 500 can allow for a patient-specific glenoid implant 102 to be created with less equipment. In some examples, before or after the bone substitute 508 has cured within the glenoid defect 104, the patient-specific glenoid implant 102 can be resurfaced as needed, for example, to create a flat surface.

Figure 6:
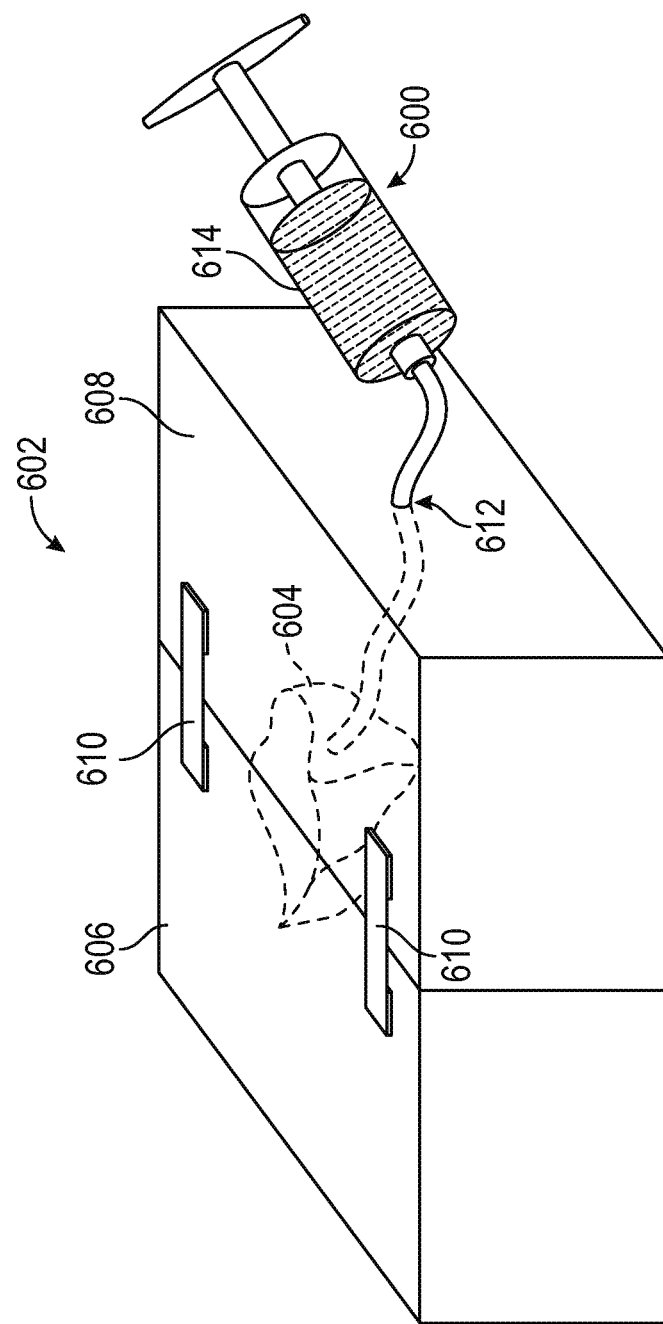
FIG. 6 is a perspective view of an injector and a patient-specific mold, in accordance with at least one example of the present disclosure.

FIG. 6 is a perspective view of an injector 600 and a patient-specific mold 602, in accordance with at least one example of the present disclosure. In at least one example, the patient-specific mold 602 can include a patient-specific void 604 corresponding to the glenoid defect 104 of the specific patient 106. In at least one example, the patient-specific void 604 can match the glenoid defect 104. In some examples, the patient-specific mold 602 can include multiple portions 606, 608 coupled together via one or more locking features 610. In at least one example, the patient-specific mold 602 can be a single unitary piece. In some examples, the patient-specific mold can include an opening 612 for receiving bone substitute 614 from the injector 600 to fill the patient-specific void 604. In at least one example, after the patient-specific void 604 is filled with the bone substitute, and the bone substitute has been allowed to cure, the one or more locking features 610 of the patient-specific mold 602 can be disengaged, and the patient-specific glenoid implant 102 can be removed from the patient-specific mold 602. In at least one example, the patient-specific glenoid implant 102 can then be implanted into the glenoid defect 104 of the specific patient 106.

Figure 7:
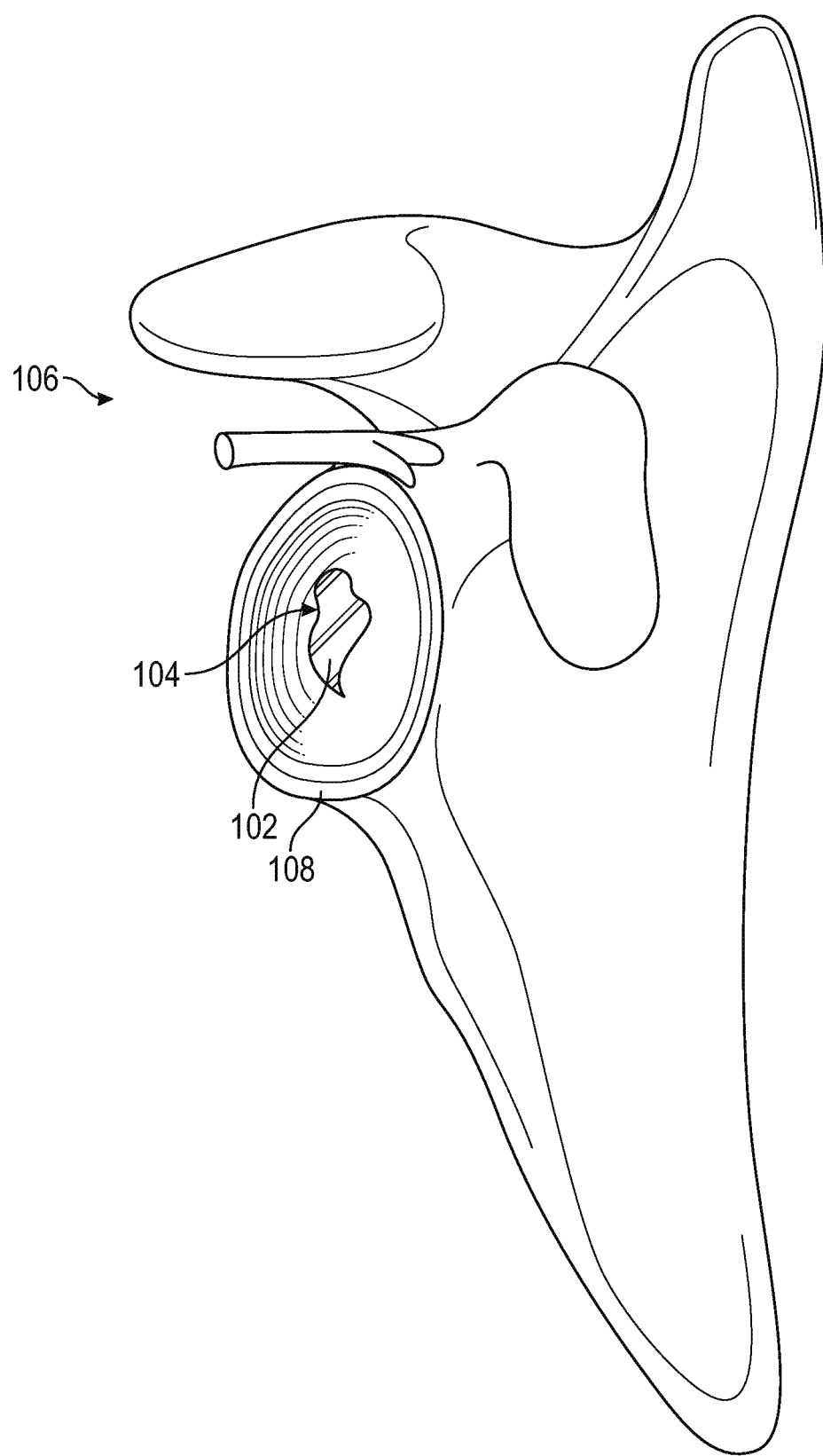
FIG. 7 is a perspective view of a patient-specific glenoid implant implanted in a corresponding glenoid defect of the specific patient, in accordance with at least one example of the present disclosure.

FIG. 7 is a perspective view of the patient-specific glenoid implant 102 implanted in the anatomy of the specific patient 106 to repair the glenoid defect 104 of the specific patient, in accordance with at least one example of the present disclosure. In some examples, the patient-specific glenoid implant 102 can be formed using any one or more of the apparatus, systems and methods described with reference to FIGS. 1-6. In at least one example, the patient-specific glenoid implant 102 can be attached to a base plate or other device before implantation into the glenoid defect 104. In some examples, the patient-specific glenoid implant can be formed of bone, for example, cancellous bone from a humeral head resection of the specific patient 106, or other bone. In some examples, the patient-specific glenoid implant can be formed of bone substitute, for example, Equivabone®, Gamma-BSM, CarriGen®, Beta-BSM, or the like. In at least on example, the patient-specific glenoid implant can be formed of osteoconductive, osteoinductive self-setting bone void filler. In at least one example, the patient-specific glenoid implant 102 can be oversized (e.g., by enlarging the geometry of the patient-specific devices) to facilitate interdigitating of the patient-specific glenoid implant 102 with the surrounding bone. In at least one example, the patient-specific glenoid implant can be provided with additional material to improve initial fixation. In at least one example, the implant material of the patient-specific glenoid implant 102 is both osteoconductive and osteoinductive.

In at least one example, the apparatus, systems and methods of FIGS. 1-7 can allow for a surgeon to precisely match a specific patient's anatomy every time, without needing to resect bone from the scapular or the latarjet. In at least one example, the apparatus, systems and methods of FIGS. 1-7 can allow for a surgeon to place a patient-specific glenoid implant without extreme difficulty. In at least one example, the apparatus, systems and methods of FIGS. 1-7 can be utilized as a two-stage process within VRS (Vault Reconstruction System), Trabecular Metal™ Reverse Shoulder System, Comprehensive® Reverse Shoulder System, PMI® (Patient Matched Implant), or other shoulder system cases. For example, the system can first be used to partially fill the glenoid defect (which can be allowed to harden or potentially to heal the bone first), then a subsequent patient-specific implant can be used to match the new shape of the glenoid (with the glenoid defect already filled). In at least one example, the allograft injection method can be followed up by anatomical glenoid systems after the bone has healed. In at least one example, the apparatus, systems and methods of FIGS. 1-7 can allow for a reduction in surgical time and better fixation, screw purchase, geometry, and overall formality within the specific patient.

In the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own as a separate example.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific examples. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific examples. However, the benefits, advantages, solutions to problems, and any feature(s) that may cause any benefit, advantage, or solution to occur or become more pronounced are not to be construed as a critical, required, or essential feature of any or all the claims. Moreover, the particular examples disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular examples disclosed above may be altered or modified and all such variations are considered within the scope of the disclosed subject matter. Accordingly, the protection sought herein is as set forth in the claims below.

What is claimed is:

1. A system for repairing a glenoid defect of a specific patient, the system comprising:
    an impactor body; and
    a patient-specific punch coupled to the impactor body, the patient-specific punch including a patient-specific void corresponding to the glenoid defect;
    wherein the impactor body is configured to drive the patient-specific punch into an implant material to form a patient-specific glenoid implant.

2. The system of claim 1, wherein the patient-specific punch is removably coupled to the impactor body.

3. The system of claim 1, wherein the implant material comprises a bone puck formed from a resected portion of a humeral head.

4. They system of claim 1, wherein the patient-specific glenoid implant is configured to be coupled to a base plate that is configured to be coupled to the glenoid.

5. The system of claim 4, further comprising:
    a patient-specific shaping block configured to receive the patient-specific glenoid implant in a shaping void; and
    a spacer configured for placement in the patient-specific shaping block, the spacer having a geometry corresponding to the base plate;
    wherein the shaping void is configured to match the glenoid defect;
    wherein the patient-specific glenoid implant is configured to be impacted such that the shaping void and the spacer shape the patient-specific glenoid implant to repair the glenoid defect.

6. The system of claim 5, further comprising:
    an impactor head configured to be removably coupled to the impactor body.

7. The system of claim 5, wherein the patient-specific shaping block further includes a cover, the cover configured to receive a guide pin.

8. The system of claim 5, further comprising a base plate reamer configured to ream the patient-specific glenoid implant to match features of the base plate.

9. The system of claim 1, wherein the patient-specific punch includes knifed edges.

10. A system for repairing a glenoid defect of a specific patient, the system comprising:
    a patient-specific punch including a patient-specific void corresponding to the glenoid defect, the patient-specific punch configured to form a patient-specific glenoid implant; and
    a patient-specific shaping block configured to receive the patient-specific glenoid implant in a shaping void that matches the glenoid defect;
    wherein the patient-specific glenoid implant is configured to be impacted such that the shaping void shapes the patient-specific glenoid implant to fill the glenoid defect.

11. The system of claim 10, further comprising:
    a base plate configured to be coupled to the patient-specific glenoid implant for implantation in the specific patient.

12. The system of claim 11, further comprising:
    a spacer configured to be inserted into the patient-specific shaping block, the spacer having a geometry corresponding to the base plate.

13. The system of claim 10, further comprising:
    a bone cutter configured to form a bone puck, wherein the patient-specific punch is configured to impact the bone puck to form the patient-specific glenoid implant.

14. The system of claim 13, wherein the bone cutter comprises:
    an extraction block configured to receive a humeral head resection;
    a fastener configured to extend through the humeral head resection; and
    a rotatable blade assembly configured to be received by, and rotate around, the fastener to cut the humeral head resection to form the bone puck.

15. The system of claim 10, further comprising:
    an impactor body comprising an attachment portion configured to be removably coupled to one or more attachments, wherein the patient-specific punch is configured to be removably coupled to the attachment portion of the impactor body.

16. The system of claim 15, further comprising:
    an impactor head attachment configured to be removably coupled to the attachment portion of the impactor body.

17. A method for repairing a glenoid defect of a specific patient, the method comprising:
    driving a patient-specific punch into an implant material to create a patient-specific glenoid implant, wherein the patient-specific punch includes a patient-specific void corresponding to the glenoid defect;
    placing the patient-specific glenoid implant in a patient-specific shaping block including a shaping void that matches the glenoid defect; and
    impacting the patient-specific glenoid implant, such that the patient-specific shaping block shapes the patient-specific implant to fill the glenoid defect.

18. The method of claim 17, further comprising:
    forming the bone puck from a resected portion of a humeral head.

19. The method of claim 17, further comprising:
    reaming the patient-specific implant to accommodate a base plate.

20. The method of claim 19, further comprising:
    coupling the patient-specific glenoid implant to the base plate that is configured to be coupled to the glenoid.

* * * * *